(12) United States Patent
Harvey

(10) Patent No.: US 6,214,367 B1
(45) Date of Patent: Apr. 10, 2001

(54) INJECTABLE COMPOSITIONS

(75) Inventor: Colin Manson Harvey, Auckland (NZ)

(73) Assignee: Ashmont Holdings Limited, Auckland (NZ)

( * ) Notice: Subject to any disclaimer, the term of this patent is extended or adjusted under 35 U.S.C. 154(b) by 0 days.

(21) Appl. No.: 09/214,260

(22) PCT Filed: Jun. 5, 1997

(86) PCT No.: PCT/NZ97/00073

§ 371 Date: Dec. 31, 1998

§ 102(e) Date: Dec. 31, 1998

(87) PCT Pub. No.: WO97/46204

PCT Pub. Date: Dec. 11, 1997

(30) Foreign Application Priority Data

Jun. 5, 1996 (NZ) .......................................... 286752
Jul. 30, 1996 (NZ) .......................................... 299093

(51) Int. Cl.$^7$ ................................. A61F 13/00; A61F 2/00
(52) U.S. Cl. ........................... 424/422; 424/424; 424/426
(58) Field of Search ..................................... 424/422, 424, 424/426

(56) References Cited

U.S. PATENT DOCUMENTS

| | | |
|---|---|---|
| 3,579,633 | 5/1971 | Thomson . |
| 4,199,569 | 4/1980 | Chabala et al. . |
| 4,292,307 | 9/1981 | Zemlyakova . |
| 4,310,519 | 1/1982 | Albers-Schonberg et al. . |
| 4,606,918 | 8/1986 | Allison et al. . |
| 4,781,920 | 11/1988 | Quinlan . |
| 5,262,400 | 11/1993 | Chu et al. . |
| 5,550,153 * | 8/1996 | Kerz ...................................... 514/460 |
| 5,639,876 * | 6/1997 | Tripp et al. ........................... 536/23.7 |
| 5,733,566 * | 3/1998 | Lewis .................................... 424/426 |

FOREIGN PATENT DOCUMENTS

| | | |
|---|---|---|
| 0 181 525 | 5/1986 | (EP) . |
| 0 215 313 | 3/1987 | (EP) . |
| 0 750 907 | 1/1997 | (EP) . |
| 1171125 | 11/1969 | (GB) . |
| 2 050 830 | 1/1981 | (GB) . |
| 183847 | 4/1977 | (NZ) . |
| 186851 | 4/1978 | (NZ) . |
| 186852 | 4/1978 | (NZ) . |
| 188459 | 9/1978 | (NZ) . |
| 188460 | 9/1978 | (NZ) . |
| 199817 | 2/1982 | (NZ) . |
| WO 94/26113 | 11/1994 | (WO) . |

OTHER PUBLICATIONS

P. Lammie et al., "Alterations in Filarial Antigen–Specific Immunologic Reactivity Following Treatment with Ivermectin and Diethylcarbamazine", Am. J. Trop. Med. Hyg., vol. 46, No. 3, 1992, pp. 292–295.

D. Fink et al., "Pharmacokinetics of Ivermectin in Animals and Humans", Ivermectin and Abamectin, Chapter 7.

Joseph R. Robinson et al., Controlled Drug Delivery Fundamentals and Applications, Second Edition, pp. 452–457.

H. Stone, "Efficacy of Experimental Animal and Vegetable Oil–Emulsion Vaccines for Newcastle Disease and Avian Influenza", Avian Diseases, vol. 37, 1993, pp. 399–405.

J. Freund et al., "Antibody Formation and Sensitization with the Aid of Adjuvants", , Apr. 13, 1948, pp. 383–398.

O. Umehara et al., "Compatability between doramectin and foot–and–mouth disease vaccine administered simultaneously to cattle", vol. 2, No. 2, 1993.

H. Akuffo et al., "Ivermectin–induced immunopotentation in onchocerciasis: recognition of selected antigens following a single dose of ivermectin", Clin. Exp. Immunol., vol. 103, 1996, pp. 244–252.

C.L. Schwartzkoff et al., "Australian Veterinary Journal", Biological Abstracts, vol. 102, Issue 009, Ref. 140304.

R. Bomford, "Adjuvants for Anti–parasite Vaccines", Parasitology Today, vol. 5, No. 2, 1989, pp. 41–46.

Cyanamid, "Cydectin Eweguard 6 in 1 Vaccine and Wormer For Adult Sheep", Animal Remedies Board, License No. A 07302.

R. Gupta et al., "Adjuvants—a balance between toxicity and adjuvanticity", Vaccine, vol. 11, Issue 3, 1993, pp. 293–306.

S. R. Wicks et al., "Effect of formulation on the pharmacokinetics and efficacy of doramectin", Veterinary Parasitology, vol. 49, 1993 pp. 17–26.

Philip J. Willson et al., "Tissue Reaction and Immunity in Swine Immunized with *Actinobacillus pleuropneumoniae* Vaccines", Can. J. Vet. Res., vol. 59, 1995, pp. 299–305.

* cited by examiner

*Primary Examiner*—Thurman K. Page
*Assistant Examiner*—Amy Pulliam
(74) *Attorney, Agent, or Firm*—Young & Thompson

(57) ABSTRACT

A stable injectable composition includes a non-aqueous parasitic agent in a therapeutically effect amount, chosen from the group of avermectin, ivermectin, doramectin, abamectin, milbemycin and moxidecting, and an antigen in combination with a liquid carrier that also acts as an adjuvant for use with warm-blooded animals and a method for treating parasitic diseases and preventing bacterial and viral diseases in warm-blooded animals.

10 Claims, No Drawings

INJECTABLE COMPOSITIONS

TECHNICAL FIELD OF THE INVENTION

This invention relates to novel compositions of macrolide avermectin and milbemycin endecticides with an immunising agent and in particular it relates to a stable injectable composition for use with warm-blooded animals, in particular ruminants.

The use of a combination of an parasitic agent and immunising agent as a single injectable formulation offers advantages both in time and cost saving to the farmer.

BACKGROUND

New Zealand Patent Nos. 191413 and 193807 of ICI Tasman Limited disclose water based formulations of D, L-tetramisole and clostridial vaccine in the treatment of helminthiasis and clostridial diseases in warm-blooded animals. Both D, L-tetramisole and the clostridial vaccine are water soluble hence a combination of the two is straight forward. What was surprising was that the clostridial vaccine remained effective at a pH lower than 6.0 and that the combination improved the immune response in ruminants, though not in other animals.

These aqueous formulations commonly used an adjuvant such as alum or alum hydroxide to enhance the effect of the antigen. Such adjuvants are usually included in the formulation as an aqueous suspensions. The vaccines can then be readily mixed with water based anthelmintic formulations.

Since the use of D, L-tetramisole and more particularly the L-isomer levamisole, there have been a number of other potent antiparasitic macrocyclic lactone compounds such as the avermectins, ivermectin, doramectin, abamectin, milbemycin, moxidectin used in the treatment of diseases in warm blooded animals. These later parasiticides are insoluble in water which creates difficulties in formulating stable injectable compositions. However, the compounds have the advantage that they are active against internal and external parasites in domestic animals.

Formulations are therefore based on co-solvent systems or aqueous solvent Systems utilising a water-soluble solvent with one or more wetting agents. Water soluble solvents mix readily with traditional aqueous adjuvant systems to form combinations of anthelmintics and vaccines. This is not the case with oil based (non-aqueous) systems.

OBJECT

It is an object of the invention to provide an improved injectable composition combining a parasitic agent and an antigen or at least one that provides the public with a useful choice.

STATEMENT OF INVENTION

It has been surprisingly discovered that non-aqueous anthelmintics can be combined with an antigen using an oil as an adjuvant and carrier to give a stable formulation that can be safely injected into warm blooded animals including cattle and sheep.

In one aspect the invention comprises a stable injectable composition comprising a non-aqueous parasitic agent in a therapeutically effect amount and an antigen in combination with a liquid carrier that also acts as an adjuvant for use with warm blooded animals.

Preferably the non-aqueous parasitic agent is a macrolide compound selected from group comprising avermectin, ivermectin, doramectin, abamectin, milbemycin and moxidectin, present in from 0.05 to 10% w/v.

More preferably the non-aqueous parasitic agent is chosen from the group comprising abamectin, ivermectin, moxidectin and doramectin.

Preferably, the carrier is an oil, either a vegetable oil such as sesame oil, saponine oil, soya bean oil, and corn oil or a mineral adjuvant oil, such as paraffin oil, or purified derivatives of vegetable or mineral oils, such as quiala, which is suitable for injection into animals or a mixture thereof. The oil acts as an adjuvant for the immunising agent and may also act as a solvent for the anthelmintic. The oil also extends the action of the parasitic agent.

Additionally, the composition may further contain an oil soluble solvent. The oil soluble solvent is chosen from the group comprising alcohols having four or more carbon atoms for example benzyl alcohol, ethylbenzyl alcohol, phenethyl alcohol and other aromatic monohydric alcohols.

Preferably the alcohol is present in the range from 10–50 w/v %.

The antigen is incorporated into the composition by emulsifying it in a suitable emulsion agent, for example sorbiten oleate (Span 80™ or Liposorb 80™). Other suitable emulsion agents may also be used. The emulsifier is present in the range of from 5–50 w/v %.

Antigens suitable to be used in the compositions include antigens derived from bacterial and viral pathogens of warm-blooded animals. Preferably the antigen is chosen from the group comprising antigens derived from and toxins of clostridial diseases including *Clostridium septicum, Clostridium tetani, Clostridium chauvoei, Clostridium novyi, Clostridium sordelli* and *Clostridium haemolytica*. Other possible antigens include Pasteurella, *Pasteurella maltocida* and *Corynebacterium pseudotuberculosis* and viral antigens for Infectious Bovine Rhinotracheitis, Bovine Viral Diarrhoea and Parainfluenza.

In another aspect, the invention comprises a method of treating parasitic diseases and preventing viral and bacterial diseases in warm blooded animals by administration to an animal of a composition as described above.

Preferably the composition is administered to the animal by injecting the animal.

Preferably the composition is administered at the rate of 0.5–5 mL/50 kg bodyweight of the animal.

PREFERRED EMBODIMENTS

The present invention will be described by way of example only with reference to the following examples.

| Formulation 1 (oil based) | |
|---|---|
| Part A | w/v % |
| Abamectin | 1.00 |
| Benzyl Alcohol | 10.0 |
| Sesame oil | 40.0 |
| Paraffin Oil | to volume |
| Part B | v/v % |
| Part A (1% abamectin) | 50.0 mls |
| Span 80 | 10 gm |

-continued

| Vaccine | to volume |
|---|---|
|  | 100% |

Formulation 2 (oil based)

| Part A | w/v % |
|---|---|
| Abamectin (or ivermectin) | 1.13 |
| Benzyl Alcohol | 20.0 |
| Sesame Oil | to volume |

| Part B | v/v % |
|---|---|
| Part A (1% abamectin) | 50.0 mls |
| Span 80 | 10 gm |
| Vaccine | to volume |
|  | 100% |

Formulation 3 (oil based)

| Part A | w/v % |
|---|---|
| Ivermectin | 1.00 |
| Benzyl Alcohol | 10.0 |
| Saponin Oil | to volume |

| Part B | v/v % |
|---|---|
| Part A | 50.0 mls |
| Span 80 | 20 gm |
| Vaccine | to volume |
|  | 100% |

Formulation 4 (oil based)

| Part A | w/v % |
|---|---|
| Doramectin | 1.13 |
| Benzyl Alcohol | 20.0 |
| Sesame Oil | to volume |

| Part B | v/v % |
|---|---|
| Part A (1% abamectin) | 50.0 mls |
| Liposorb 80 | 10 gm |
| Vaccine | to volume |
|  | 100% |

Formulation 5 (oil based)

| Part A | w/v % |
|---|---|
| Abamectin | 1.13 |
| Benzyl Alcohol | 20.0 |
| Sesame Oil | to volume |

| Part B | v/v % |
|---|---|
| Part A | 50.0 ml |
| Sorbitan Oleate | 10 gm |
| Antigen 1 | 4.555 ml |
| Antigen 2 | 0.135 ml |
| Antigen 3 | 0.870 ml |
| Antigen 4 | 0.933 ml |
| Antigen 5 | 4.258 ml |
| Benzyl Alcohol | to volume |
|  | 100% |

Dosage rates for these formulations range from 0.5–5 ml/50 kg bodyweight of the animal.

These preparations have been shown to be stable and do not cause injury when injected to warm blooded animals. The parasitic agent and the antigen retain their activity. The formulations have a shelf life of approximately two years.

We have found that a formulation of a parasitic agent and an antigen, such as a clostridial antigen, containing an oil such as sesame oil as the solvent is effective in the treatment of helminthiasis and clostridial diseases in warm blooded animals. Suprisingly, the oil also acts as an adjuvant in the composition, enhancing the activity of the vaccine and extending the parasiticide activity of the anthelmintic. Compositions that contained a traditional adjuvant such as alum and the oil stimulated the working of the vaccine to such a level that an adverse reaction was produced in the animal.

Advantages

The compositions of the invention are stable and be stored for long periods of time without loss of either parasitic agent or antigen potency.

Industrial Application

The formulations shown above are effective in the treatment of parasitic diseases and the prevention of bacterial and viral diseases in warm blooded animals, including but not limited to cattle and sheep.

Variations

Although the above examples use abamectin, ivermectin or doramectin, it is possible to use the other anthelmintics of the macrolide group.

Although the use of a clostridial vaccine as the antigen is preferred a variety of other antigens effective against other bacterial or viral pathogens could be incorporated.

Although sesame oil is preferred as the solubilising agent, other oils such as soya bean oil, corn oil or mineral adjuvant oils, such as paraffin oils, or suitable mixtures thereof, may be used.

Finally, it will be appreciated a that a variety of other alterations and modifications may be made to the forgoing without departing from the spirit and scope of the invention.

What is claimed is:

1. A stable injectable composition suitable for the treatment of warm-blooded animals consisting essentially of:
    a non-microencapsulated and non-aqueous macrolide compound present in a therapeutically effective amount, chosen from the macrolide group of milbemycins and avermectins compounds; and
    an antigen in combination with a liquid carrier that also acts as an adjuvant for use with the warm-blooded animals, the carrier including one or more oils selected from the group of vegetable or mineral oils and purified derivatives thereof.

2. A composition as claimed in claim 1 wherein the non-aqueous macrolide compound is present in from 0.05–10 w/v %.

3. A composition as claimed in claim 1 wherein the non-aqueous macrolide compound is chosen from the group comprising abamectin, ivermectin, moxidectin and doramectin.

4. A composition as claimed in claim 1 wherein the carrier oil or mixture of oils is suitable for injection into animals and is chosen from the group comprising sesame oil, saponine oil, soya bean oil, corn oil, paraffin oils, purified derivatives of vegetable oils and mineral adjuvant oils and mixtures thereof, and wherein the carrier extends the activity of the parasitic agent.

5. A composition as claimed in claim 1 further containing an oil soluble solvent chosen from the group comprising alcohols having four or more carbon atoms and the oil soluble solvent is present in a range from 10–50 w/v %.

6. A composition as claimed in claim 1 further containing an emulsifier and the emulsifier is present in the range of from 5–50 w/v %.

7. A composition as claimed in claim 1 wherein the antigen is chosen from the group comprising antigens and toxins for the prevention of clostridial diseases in warm-blooded animals.

8. A method of treating parasitic diseases and treating bacterial and viral diseases in warm blooded animals by administration to an animal of a composition consisting essentially of:

a non-microencapsulated and non-aqueous macrolide compound present in a therapeutically effective amount, chosen from the macrolide group of milbemycins and avermectins compounds; and an antigen in combination with a liquid carrier that also acts as an adjuvant for use with the warm-blooded animals, the carrier including one or more oils selected from the group of vegetable or mineral oils and purified derivatives thereof.

9. A method as claimed in claim 8 wherein the composition is administered to the animal by injecting the animal.

10. A method as claimed in claim 8 wherein the composition is administered at the rate of 0.5–5 mL/50 kg bodyweight of the animal.

* * * * *